(12) United States Patent
Shaughnessy et al.

(10) Patent No.: US 6,998,123 B1
(45) Date of Patent: Feb. 14, 2006

(54) OSTEOPOROSIS TREATMENT WITH ANTI-IL-11 ANTIBODY

(76) Inventors: Stephen Shaughnessy, 72 Leaside Drive, St. Catharines, Ontario (CA) L8V 1C3; Richard Carl Austin, 68 Rosemary Lane, Ancaster, Ontario (CA) L9G 2K5

( * ) Notice: Subject to any disclaimer, the term of this patent is extended or adjusted under 35 U.S.C. 154(b) by 0 days.

(21) Appl. No.: 09/491,982

(22) Filed: Jan. 27, 2000

Related U.S. Application Data

(63) Continuation-in-part of application No. 09/314,152, filed on May 19, 1999, now abandoned.

(30) Foreign Application Priority Data

May 19, 1998  (CA) .................................. 2237915

(51) Int. Cl.
  *A61K 39/395* (2006.01)
(52) U.S. Cl. ................. 424/130.1; 424/133.1; 424/141.1; 424/145.1; 424/142.1
(58) Field of Classification Search ............. 424/85.2, 424/130.1, 133.1, 141.1, 145.1, 142.1; 435/7.1; 514/12; 530/324, 300, 350
  See application file for complete search history.

(56) References Cited

U.S. PATENT DOCUMENTS

| 5,215,895 | A |   | 6/1993  | Bennett ................... 435/69.52 |
| 5,270,181 | A |   | 12/1993 | McCoy ...................... 435/69.7  |
| 5,292,646 | A |   | 3/1994  | McCoy ...................... 435/69.7  |
| 5,530,101 | A | * | 6/1996  | Queen et al. ............ 530/387.3   |
| 5,888,510 | A | * | 3/1999  | Kishimoto et al. ...... 424/141.1    |

FOREIGN PATENT DOCUMENTS

| CA |     2177837 | 6/1996  |
| WO | WO 96/18648 | 6/1996  |
| WO | WO 96/19574 | 6/1996  |
| WO | WO 98/15283 | 4/1998  |
| WO | WO 99/59608 | 11/1999 |

OTHER PUBLICATIONS

Van Leuven et al., Genomics 1996, 31(1):65.
Karow et al., BiochemJ. 1996, 318:489.
Teramura et al., Blood 1992, 79:327.
Girasole et al,. J. Clin. Invest. 1994, 93:1516.
Tamaru et al. Proc. Natl. Acad. Sci. 1993, 90:11924.
Davis et al., Science, 1993, 260:1805.
Yin et al., The Journal of Immunology, 1993, 151(5):2555.
Ishimi et al., The Journal of Immunology, 1990, 145(10): 3297.
Vlasselaer, Progress in Growth Factor Research, 1992, 4: 337.
Kim et al., Journal of Bone and Mineral Research, 1997, 12(6):896.
Muir et al., Blood, 1997, 89(9):3236.
Muir et al., Blood, 1996, 88(4):1314.
Austin et al., FEBS Letters, 1991, 280(2):254.
Nandurkar et al., Blood, 1997, 90(6):2148.
Whitehorn et al., Biotechnology, 1995, 13(11):1215.
Leahy et al., Biotechniques, 1992, 13(5):738.
Romas et al., J. Exp. Med, 1996, 183:2581.
Ershier et al., Developmental & Comparative Immunology, 1997, 21(6):487.
Michalon et al., Biochem Biophys Res Commun, 1990, 167(1):9.
Poli et al., The EMBO Journal, 1994, 13(5):1189.
Musashi et al., Proc. Natl. Acad. Sci. U.S.A. 1991, 88:765.

\* cited by examiner

*Primary Examiner*—Prema Mertz
(74) *Attorney, Agent, or Firm*—Matthew P. Vincent; Yu Lu; Fish & Neave IP Group Ropes & Gray LLP

(57) ABSTRACT

There is disclosed a process of treating or alleviating the symptoms of pathological conditions in which bone density is decreased, which comprises inhibiting, in a mammalian patient suffering from such a condition, the formation in vivo of a tertiary complex of IL-11, its cell surface membrane receptor and the cell surface glycoprotein gp130. Examples of such substances are recombinant soluble IL-11 receptor mutants modified, as compared with native IL-11 receptor, at their gp130 binding site, and peptides which can interact with IL-11. The process of the invention not only inhibits bone resorption and hence bone loss, but also increases the process of bone formation to increase bone density.

11 Claims, 13 Drawing Sheets

SEQ ID NO. 3

```
ATGAGCAGC AGCTGCTCAG GGCTGAGCAG GGTCCTGGTG GCCGTGGCTA CAGCCCTGGT
GTCTGCCTCC TCCCCCTGCC CCCAGGCCTG GGCCCCCCA GGGGTCCAGT ATGGGCAGCC
AGGGAGGTCC GTGAAGCTGT GTTGTCCTGG AGTGACTGCC GGGGACCCAG TGTCCTGGTT
TCGGGATGGG GAGCCAAAGC TGCTCCAGGG ACCTGACTCT GGGCTAGGGC ATGAACTGGT
CCTGGCCCAG GCAGACAGCA CTGATGAGGG CACCTACATC TGCCAGACCC TGGATGGTGC
ACTTGGGGGC ACAGTGACCC TGCAGCTGGG CTACCCTCCA GCCCGCCCTG TTGTCTCCTG
CCAAGCAGCC GACTATGAGA ACTTCTCTTG CACTTGGAGT CCCAGCCAGA TCAGCGGTTT
ACCCACCCGC TACCTCACCT CCTACAGGAA GAAGACAGTC CTAGGAGCTG ATAGCCAGAG
GAGGAGTCCA TCCACAGGGC CCTGGCCATG CCCACAGGAT CCCCTAGGGG CTGCCCGCTG
TGTTGTCCAC GGGGCTGAGT TCTGGAGCCA GTACCGGATT AATGTGACTG AGGTGAACCC
ACTGGGTGCC AGCACACGCC TGCTGGATGT GAGCTTGCAG AGCATCTTGC GCCCTGACCC
ACCCCAGGGC CTGCGGGTAG AGTCAGTACC AGGTTACCCC CGACGCCTGC GAGCCAGCTG
GACATACCCT GCCTCCTGGC CGTGCCAGCC CCACTTCCTG CTCAAGTTCC GTTTGCAGTA
CCGTCCGGCG CAGCATCCAG CCTGGTCCAC GGTGGAGCCA GCTGGACTGG AGGAGGTGAT
CACAGATGCT GTGGCTGGGC TGCCCCATGC TGTACGAGTC AGTGCCCGGG ACTTTCTAGA
TGCTGGCACC TGGAGCACCT GGAGCCCGGA GGCCTGGGGA ACTCCGAGCA CTGGGACCAT
ACCAAAGGAG ATACCAGCAT GGGGCCAGCT ACACACGCAG CCAGAGGTGG AGCCTCAGGT
GGACAGCCCT GCTCCTCCAA GGCCCTCCCT CCAACCACAC CCTCGGCTAC TTGATCACAG
GGACTCTGTG GAGCAGCTGG TGCCACGCGG TTCTCATCAC CATCATCACC ACTGA
```

Fig. 1B

```
282 283 284 285 286 287 288 289 290 291
 -D- A- V- A- G- L- P- H- A- V-    NATIVE
  ↓  ↓     ↓     ↓     ↓  ↓
 -G- D- V- A- D- L- P- Y- A- L-    MUTANT    SEQ ID NO. 4
```

Fig. 2

```
MSSSCSGLSRVLVAVATALVSASSPCPQAWGPPGVQYGQPGRSVKLCCP
GVTAGDPVSWFRDGEPKLLQGPDSGLGHELVLAQADSTDEGTYICQTL
DGALGGTVTLQLGYPPARPVVSCQAADYENFSCTWSPSQISGLPTRYLT
SYRKKTVLGADSQRRSPSTGPWPCPQDPLGAARCVVHGAEFWSQYRIN
VTEVNPLGASTRLLDVSLQSILRPDPPQGLRVESVPGYPRRLRASWTYP
ASWPCQPHFLLKFRLQYRPAQHPAWSTVEPAGLEEVITDAVAGLPHAV
RVSARDFLDAGTWSTWSPEAWGTPSTGTIPKEIPAWGQLHTQPEVEPQV
DSPAPPRPSLQPHPRLLDHRDSVEQVAVLASLGILSFLGLVAGALALGL
WLRRRGGKDGSPKPGFLASVIPVDRRPGAPNL
```

*BOLDED AMINO ACIDS: HUMAN INTERLEUKIN 11 RECEPTOR PROTEIN
               SEQUENCE THAT INTERACTS WITH INTERLEUKIN 11

Fig. 3

| | PEPTIDE | PEPTIDE SEQUENCE | ANTAGONISTIC ACTIVITY |
|---|---|---|---|
| SEQ ID NO. 1 | 1 | RRLRASWTYPASWPCQPHFL | YES |
| SEQ ID NO. 2 | 2 | TYPASWPCQPHFLLKFRLQY | NO |

Fig. 4

OSTEOPOROSIS TREATMENT WITH ANTI-IL-11 ANTIBODY

CROSS-REFERENCED TO RELATED APPLICATION

This is a continuation-in-part of U.S. patent application Ser. No. 09/314,152 filed May 19, 1999, ABN.

FIELD OF THE INVENTION

This invention relates to medical treatments and to agents useful therein. More particularly, it relates to the prevention and treatment of pathological conditions in which the underlying pathology is an increase in bone resorption leading to bone loss, for example postmenopausal osteoporosis. It also relates to therapeutic agents useful in treatment and prevention of such conditions.

BACKGROUND OF THE INVENTION

The remodelling of bone depends on a balance between bone formation and bone resorption. Osteoblasts are responsible for the formation of new bone osteoid, composed mainly of nonmineralized type 1 collagen. Bone resorption is mediated by large multinucleated cells called osteoclasts. To resorb bone, osteoclasts first establish zones of close contact with the mineralized matrix. This forms a protected compartment between the osteoclast and the bone matrix interface in which an acidic microenvironment is formed. Within these zones bone is demineralized, and the collagen fibres resorbed by the action of secreted lysosomal hydrolases. A number of factors have been shown to be potent stimulators of bone resorption both in vitro and in vivo. These include parathyroid hormone, 1,25-dihydroxyvitamin $D_3$ prostaglandin-$E_2$ or -$I_2$, IL-1, TNF-$\alpha$, TNF-$\beta$ and bone-derived growth factors. None of these factors directly affect osteoclastic function; all require the presence of osteoblasts.

Increased bone resorption is a hallmark of a variety of clinical conditions. Thus, it occurs not only in postmenopausal women but is also a frequent complication of metastatic bone cancer, myeloma, and Paget's disease of bone. Current treatment involves the use of agents that block bone resorption (such as bisphosphonates and calcitonin) or, in the case of postmenopausal osteoporosis, hormone replacement therapy with estrogens.

Interleukin-11 (IL-11) has a role, either alone or in combination with other cytokines, in bone formation/resorption.

IL-11 belongs to a family of cytokines which includes interleukin-6 (IL-6), leukemia inhibitory factor (LIF), and oncostatin M(OSM). These cytokines have similar tertiary structures, share a common signal transducer (gp130) and have overlapping biological activities. In order for these cytokines to elicit a biological response, a tertiary complex, comprising the cytokine, its specific receptor (alpha chain), and gp130 must be formed.

BRIEF REFERENCE TO THE PRIOR ART

Van Leuven et al., Genomics (1996) Jan. 1; 31(1):65–70 report cloning the human gene for the interleukin-11 receptor (IL-11R), analysing the structure of the gene, and determining the predicted protein sequence. No analysis of protein structure and function was reported.

Karow et al., Biochem J. (1996) 318: 489–495, report cloning the gene for IL-11$\alpha$ receptor and elucidation of its amino acid sequence, report the production of a soluble form of murine interleukin-11 receptor (IL-11R) and demonstrate that it interacts with the IL-11 ligand with high affinity. The affinity of IL-11 alone for gp130 is reported to be below the level of detection, but a complex of IL-11 and soluble IL-11R interacts with gp130 with high affinity. The receptor is a transmembrane protein that exhibits sequence homology with other members of the haemopoietin receptor family. However, the location of the IL-11 and gp130 binding sites on the IL-11R was not disclosed.

Teramura et al. Blood 1992, 79:327 and Musashi et al. Proc. Natl. Acad. Sci. U.S.A. 1991, 88:765 report that in bone, IL-11 functions alone or in combination with other cytokines to support granulocyte/macrophage colony formation and to increase the number and ploidy of platelet-forming cells, megakaryocytes.

Girasole et al. J. Clin. Invest. 1994,93:1516 and Tamura et al. Proc. Natl. Acad. Sci. 1993,90:11924) report experimental work that demonstrates a role for IL-11 as well as other members of this family of cytokines in the process of osteoclastogenesis.

U.S. Pat. No. 5,215,895 Bennett et al., issued Jun. 1, 1993, discloses processes for production of IL-11, by culturing a cell transformed with a DNA sequence coding for IL-11.

Canadian Patent Application 2,177,837 Ciliberto et al. discloses an IL-6 antagonist which has been mutated at its gp130 binding region.

SUMMARY OF THE INVENTION

It is an object of the present invention to provide a novel procedure for treatment and for alleviation of the symptoms of clinical conditions, such as osteoporosis, in which increased bone resorption or decreased bone formation is the underlying pathology.

It is a further object of the invention to provide novel therapeutic substances useful in the treatment of such clinical conditions and/or in the alleviation of symptoms thereof.

The present invention is based upon the elucidation of the role of the cytokine interleukin-11 (IL-11) in both the process of bone resorption and the process of bone formation, and the unexpectedly advantageous results to be obtained by inhibiting its actions. This cytokine has been found to be critical for osteoclast formation and activity and therefore bone resorption. Moreover, this cytokine has been found to act as an inhibitor of bone formation. The mode of action of IL-11 in its role in bone loss conditions involves the formation of a tertiary complex of IL-11, its cell surface membrane receptor (IL-11R) and the cell surface glycoprotein gp130 (gp130). If this tertiary complex is not formed, or is formed to only a lesser extent, bone resorption is not only inhibited, but in many cases the formation of new bone is promoted, so that effectively new bone is formed and bone density is increased.

Accordingly, the present invention from one broad aspect provides a process of treating or alleviating the symptoms of a pathological condition in which bone density is decreased, which comprises inhibiting, in a mammalian patient suffering from such a condition, the formation in vivo of a tertiary complex of IL-11, IL-11R and gp130. Such conditions include those involving increased bone resorption and lack of desirable bone formation. In addition to osteoporosis, these conditions include metastatic bone cancer, myeloma, Paget's disease of bone, and bone fracture healing, especially in the elderly human patient.

According to another aspect of the invention, there are provided therapeutic agents for administration to a mammalian patient to alleviate the symptoms of pathological conditions in which bone density is decreased, and comprising biologically acceptable peptide compounds, protein sequences, small molecules and antibodies capable of interfering with the in vivo formation of a tertiary complex of IL-11, its cell surface membrane receptor IL-11R, and the cell surface glycoprotein gp130.

According to another aspect of the invention there is provided a novel use of the TRAP and bone nodule formation assays to allow the detection of IL-11 antagonists.

According to another aspect of the invention there are provided methods for the selective removal of IL-11 from a solution and methods for the purification or enrichment of IL-11 from solutions.

According to another aspect of the invention, there are provided therapeutic agents for administration to a mammalian patient to alleviate the symptoms of pathological conditions in which bone density is decreased, and comprising biologically acceptable IL-11 antagonists capable of interfering with the in vivo formation of a tertiary complex of IL-11, its cell surface membrane receptor IL-11R, and the cell surface glycoprotein gp130.

According to another aspect of the invention, there are provided therapeutic agents for administration to a mammalian patient to alleviate the symptoms of pathological conditions in which bone density is decreased, and comprising transcribable genetic materials including antisense nucleic acids capable of inhibiting the translation of a component necessary to the formation of the IL-11/IL-11R/gp130 tertiary complex.

According to another aspect of the invention, there are provided therapeutic agents for administration to a mammalian patient to alleviate the symptoms of pathological conditions in which bone density is decreased, and comprising expressible genetic materials including transcribable genetic materials encoding amino acid sequences capable of inhibiting the formation of the IL-11/IL-11R/gp130 tertiary complex.

BRIEF REFERENCE TO THE DRAWINGS

FIG. 1B is a representation of cDNA sequence depicted in SEQ ID NO. 3 and employed in Example 3, below.

FIG. 2 is a detailed sequence of the gp130 binding region of native IL-11R and indicating the specifically preferred mutation sites and mutations of the products of the present invention. The extensively mutated sequence disclosed is SEQ ID NO. 4.

FIG. 3 is a representation of a portion of the IL-11 receptor peptide sequence indicating in bold the region of interaction with IL-11.

FIG. 4 is a representation of the sequence of peptide 1 (SEQ ID NO. 1) and peptide 2 (SEQ ID NO. 2) used in Example 5 below, indicating the activity observed in that experiment.

Figure 6A:
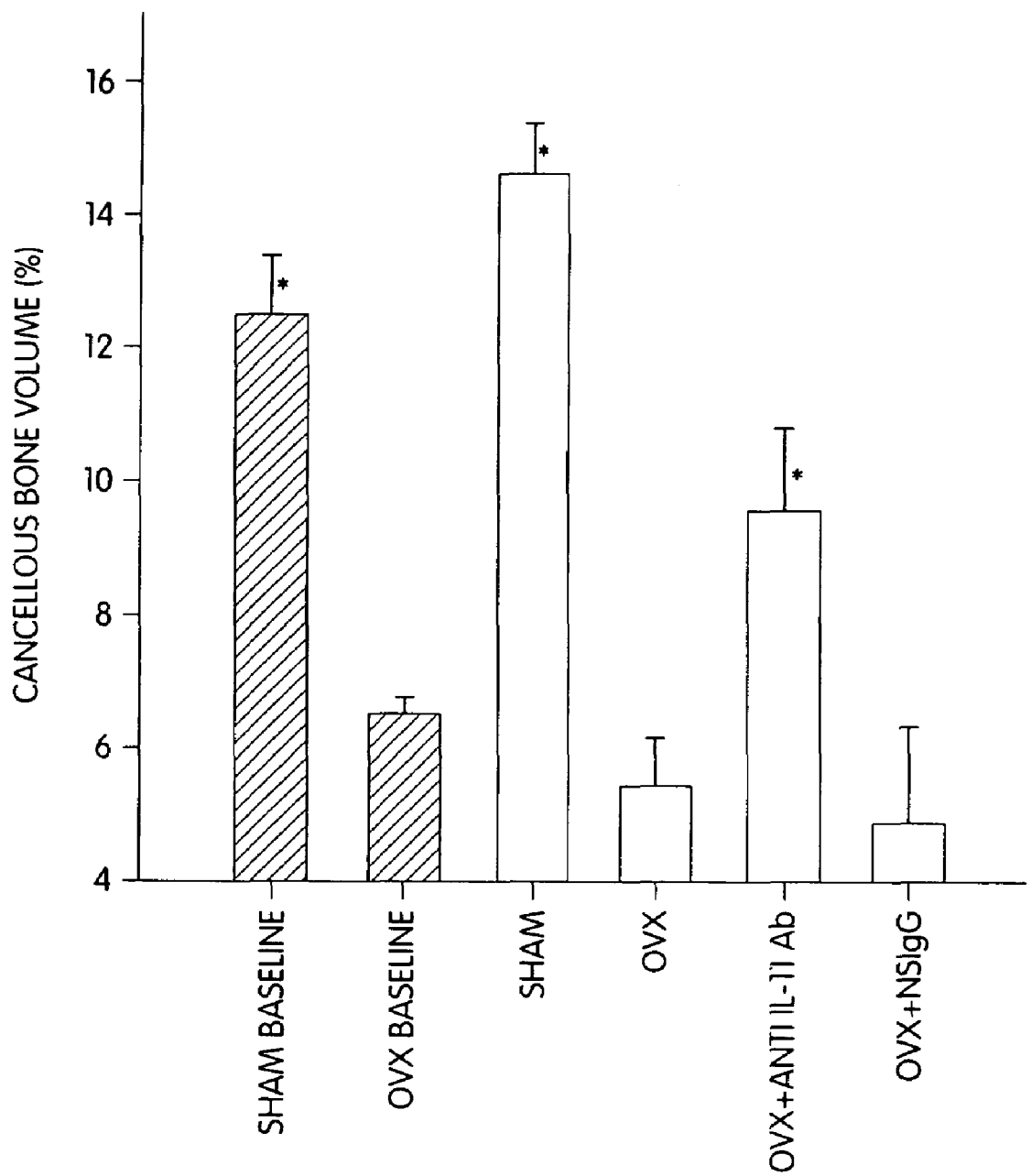
Figure 6B:
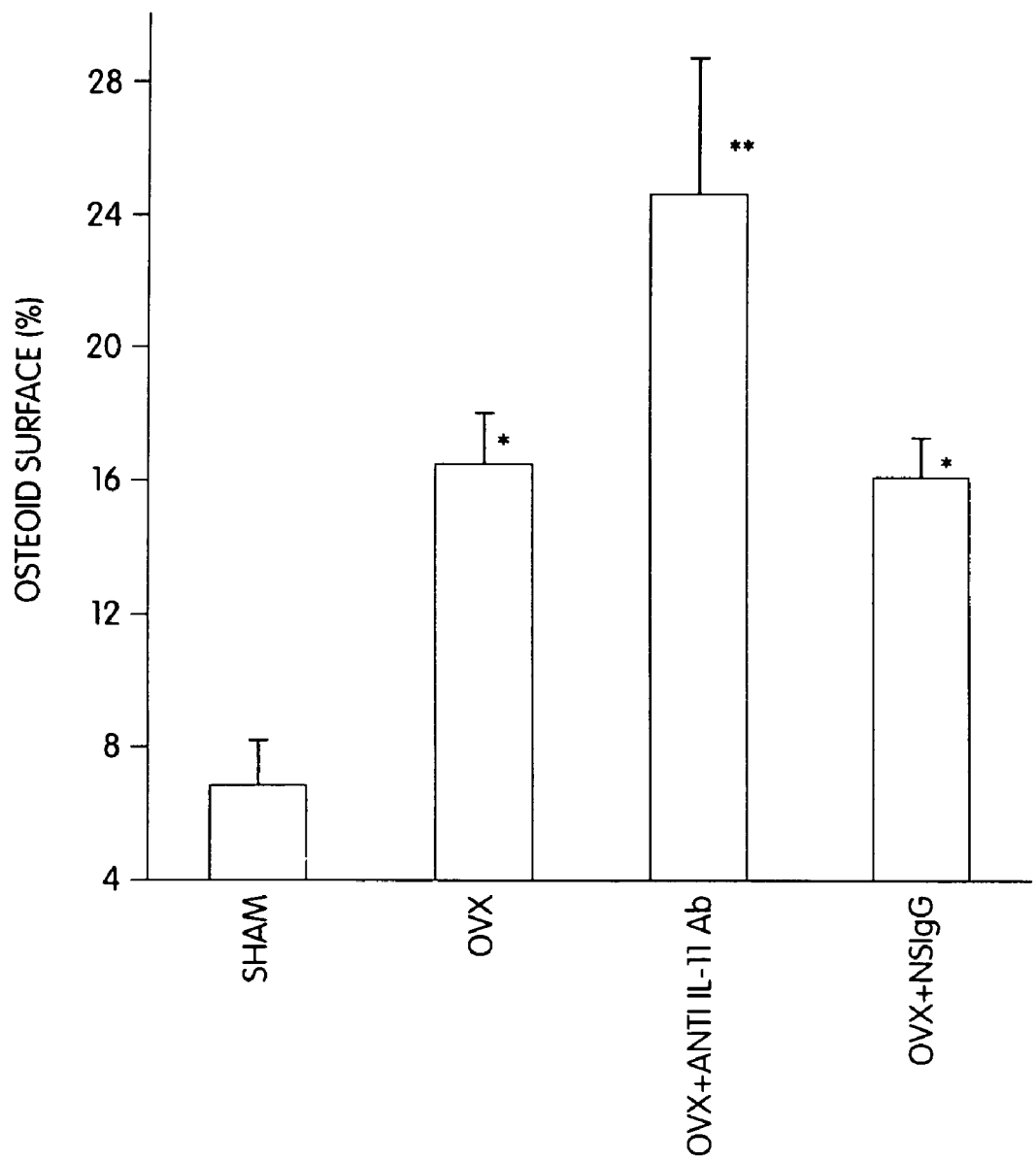
Figure 6C:
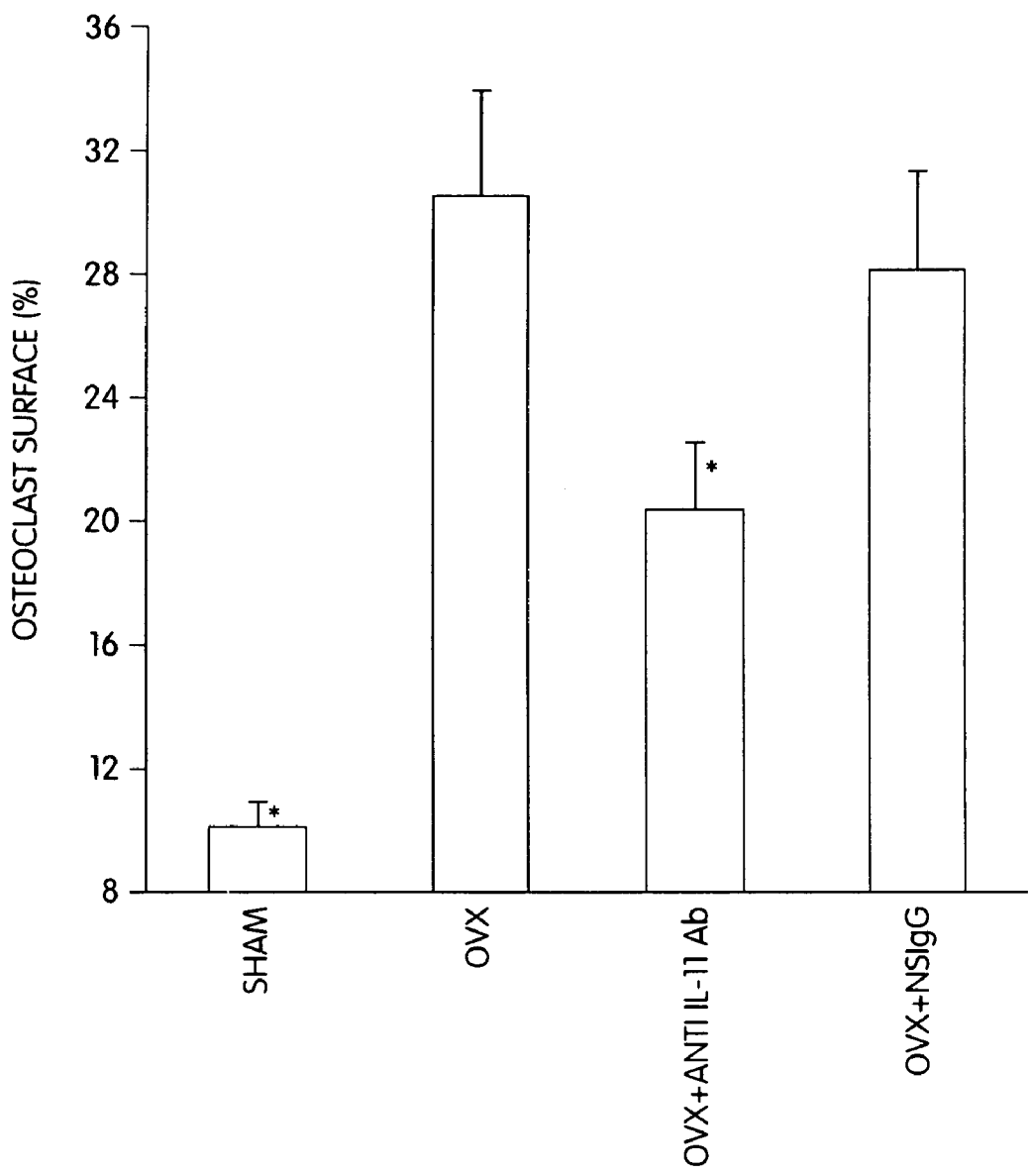

FIGS. 6 A, B and C are graphical presentations of the results obtained according to Example 2 below.

Figure 7A:
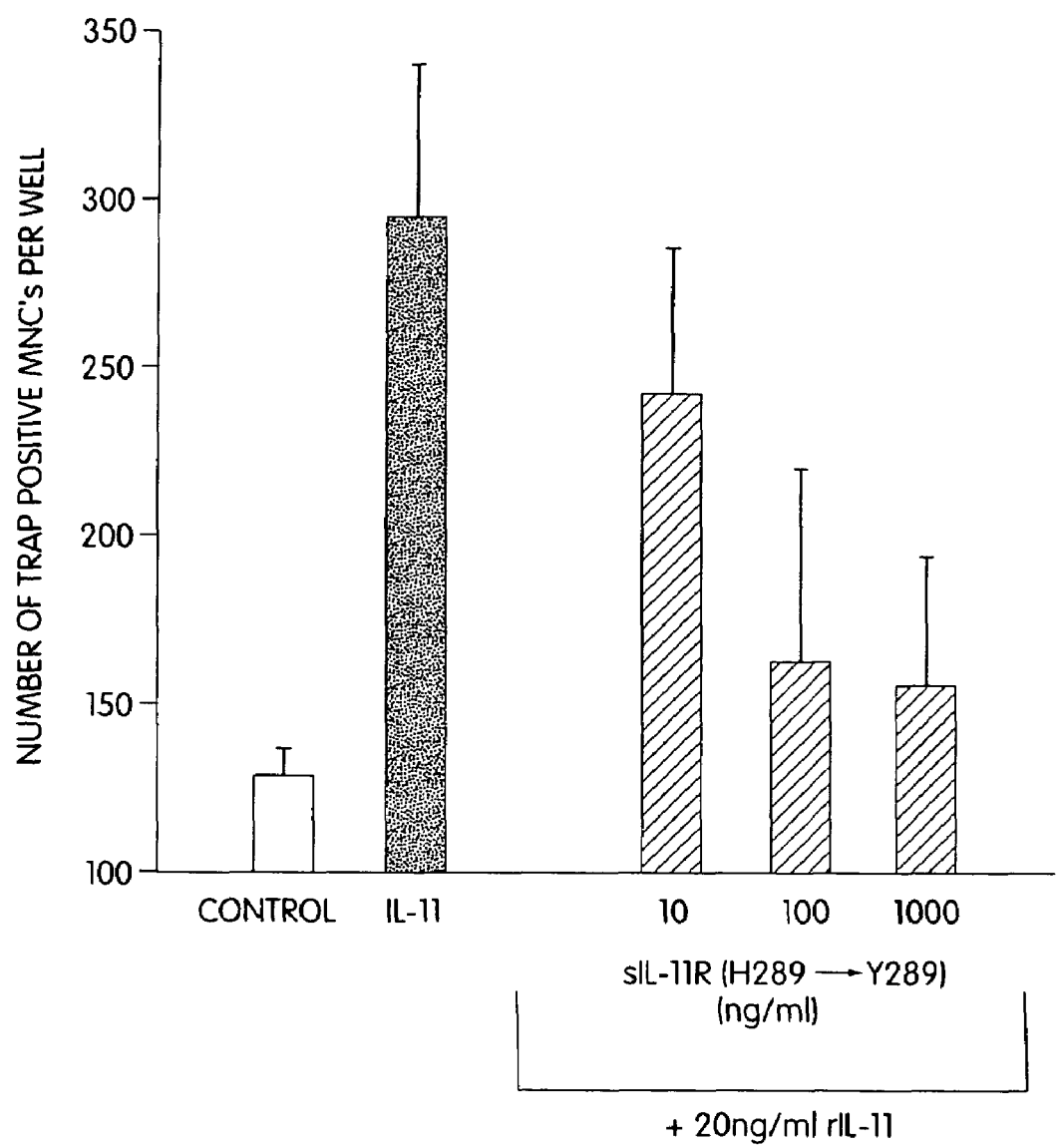
Figure 7B:
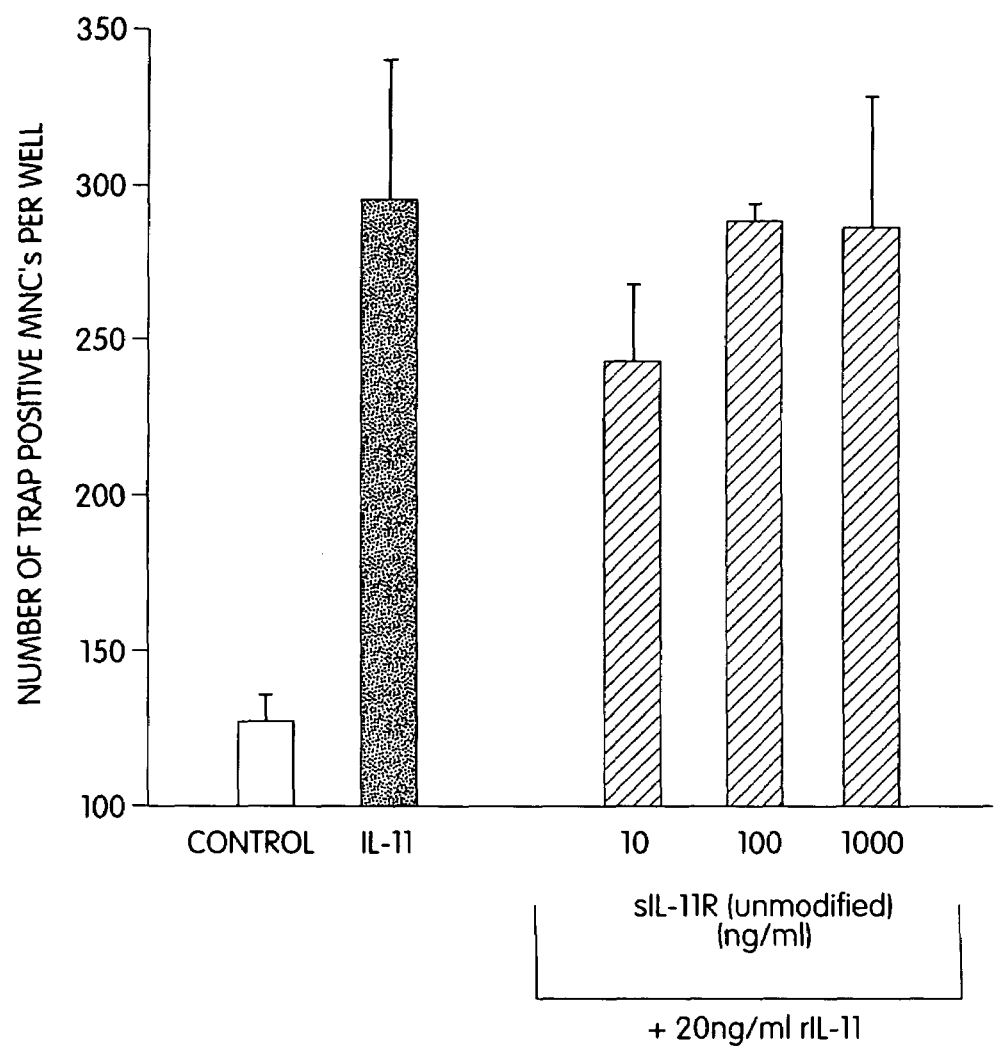

FIGS. 7 A and B are graphical presentations of the results obtained according to Example 4 below.

Figure 8:
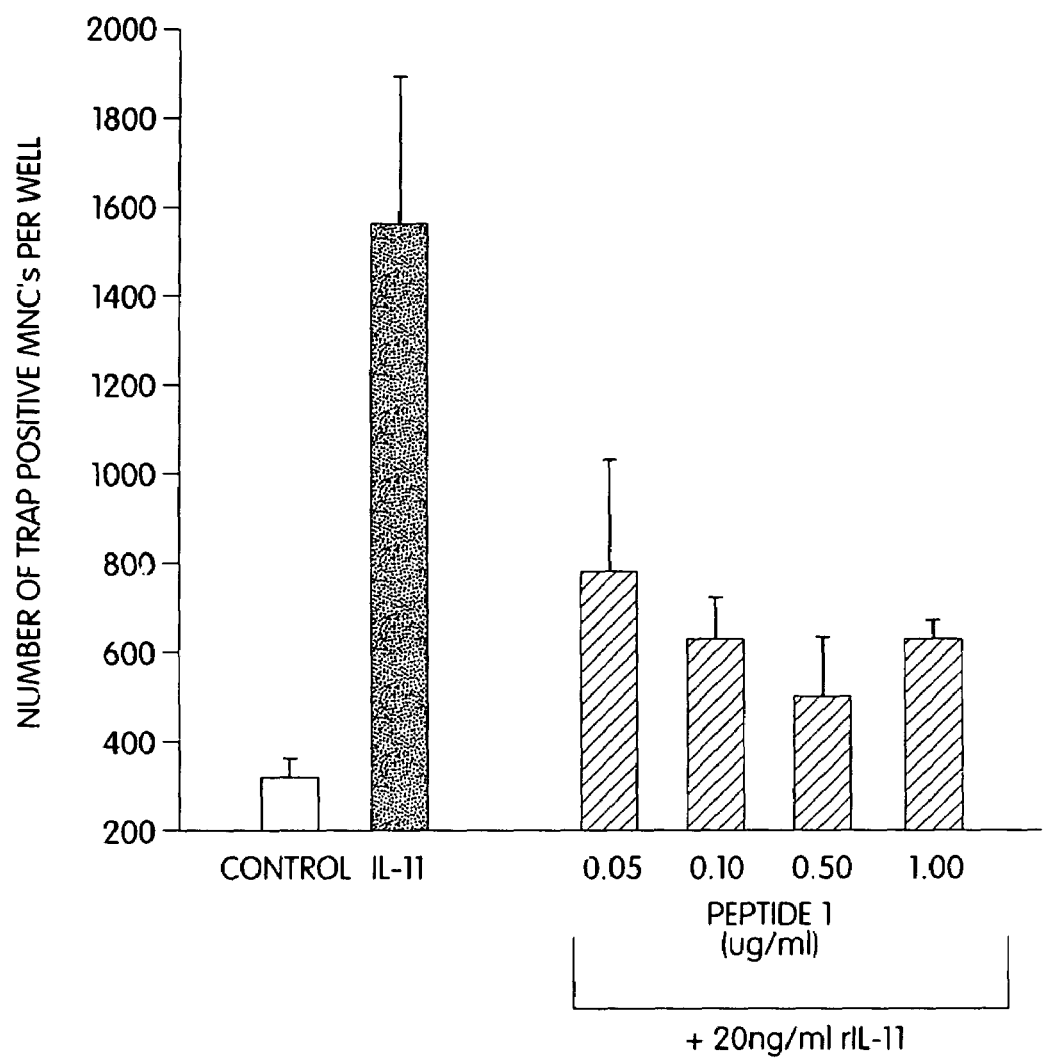

FIG. 8 is a graphical presentation of the results obtained according to Example 5 below.

Figure 9:
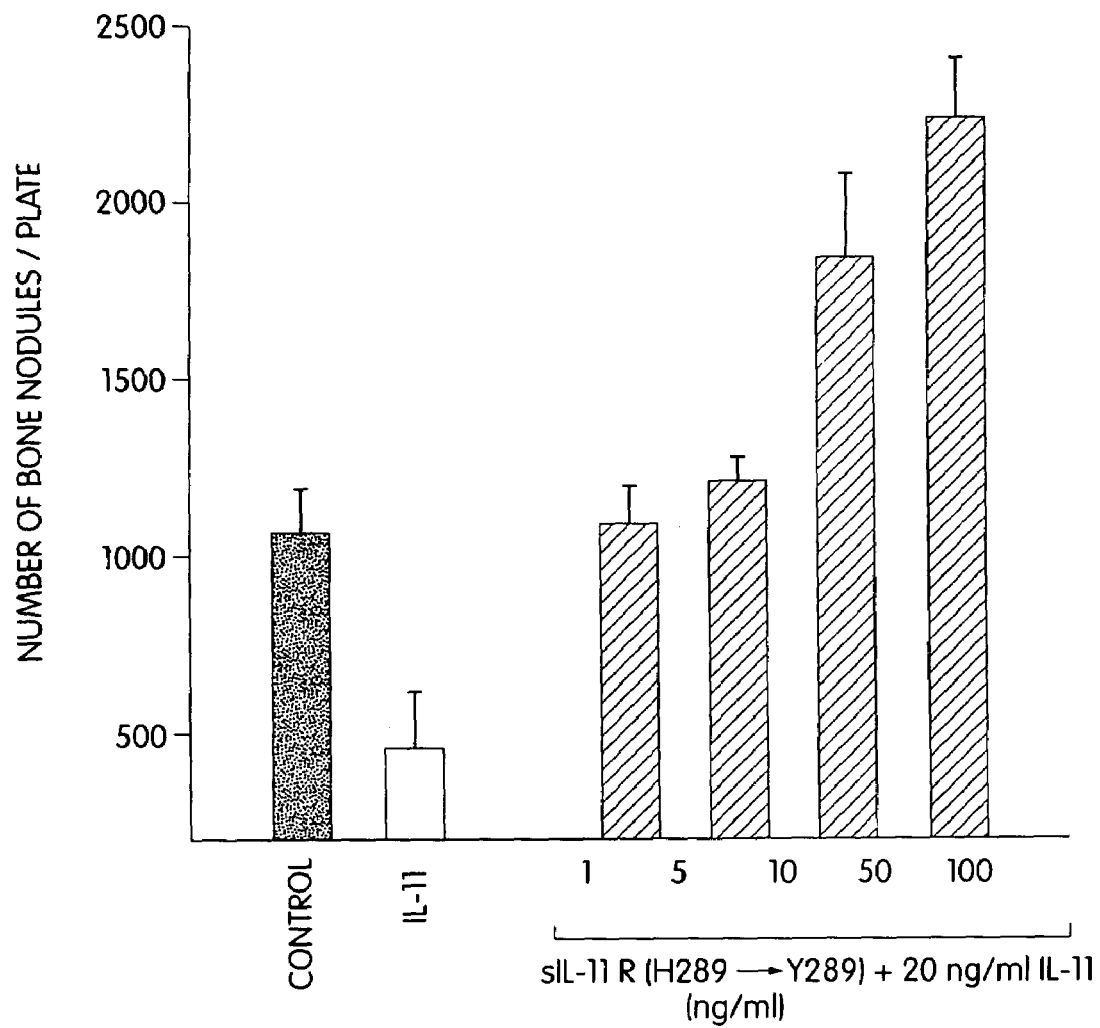

FIG. 9 is a graphical presentations of the results obtained according to Example 6 below.

Figure 10:
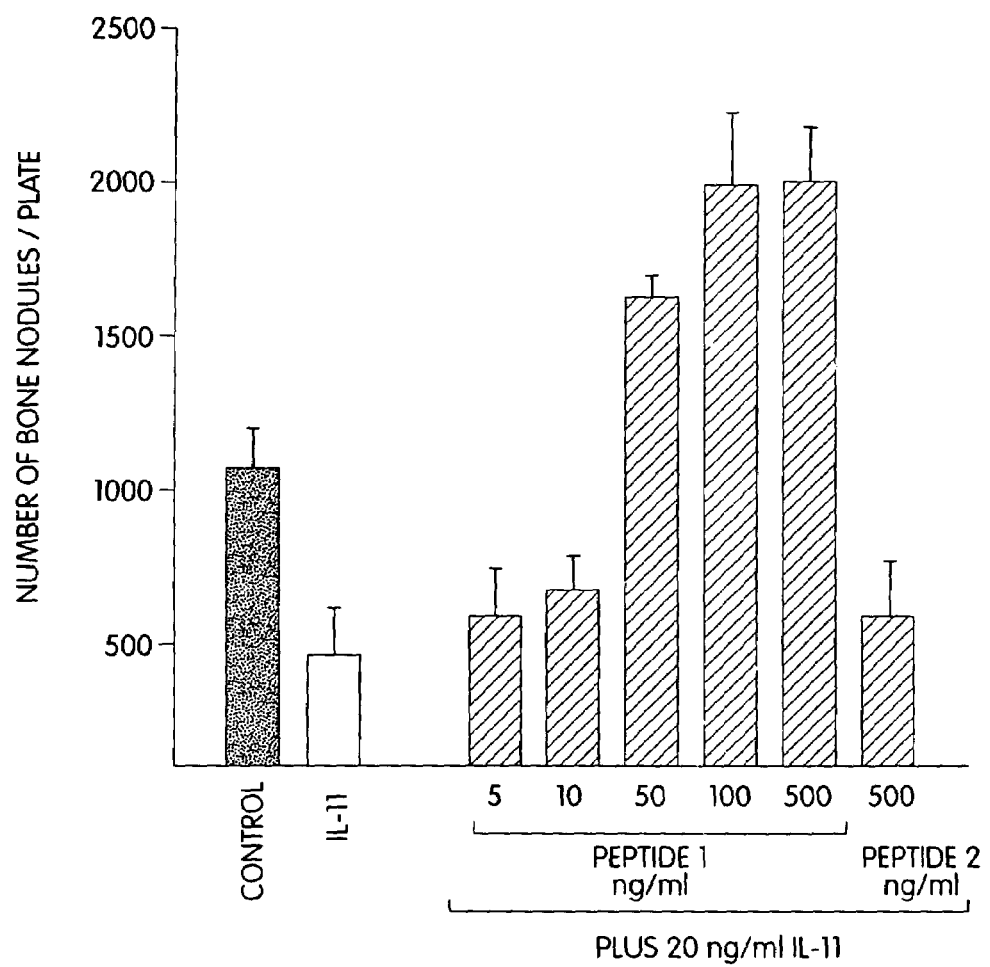

FIG. 10 is a graphical presentation of the results obtained according to Example 7 below.

DESCRIPTION OF THE PREFERRED EMBODIMENTS

The preferred process according to the invention comprises treating or alleviating the symptoms of a pathological condition in which bone density is decreased in a mammalian patient suffering from such a condition, by administering to the patient an effective amount of a substance which inhibits the in vivo formation of a tertiary complex of IL-11, its cell surface membrane receptor IL-11R and the cell surface glycoprotein gp130. Examples of such substances include antibodies to IL-11, antibodies to IL-11R, antibodies to gp130, mutant forms of IL-11 receptor, small molecule antagonists of IL-11, and peptide compounds which include sequences which selectively interact with IL-11 in the region normally bound by IL-11R, so as to interfere with the normal interaction between IL-11 and IL-11R.

One group of preferred compounds of the present invention are recombinant soluble IL-11R mutants which are modified, as compared with native IL-11R, so that they can participate in the IL-11/IL-11R interaction but do not productively interact with gp130. As a result, the tertiary complex of IL-11, IL-11R and gp130 is not formed, or is formed only to a lesser extent, so that there is no, or a lesser, biological response. In a preferred embodiment, amino acid substitutions in the gp130 binding region, in these preferred compounds, substantially or completely abolish IL-11R interactions with gp130, while having little or no effect on IL-11 binding. However, mutations in other regions of the IL-11R protein can alter the characteristics of the gp130 binding site on IL-11R and prevent or inhibit productive IL-11R/gp130 interaction. Any and all soluble IL-11 receptor mutants which interfere with the formation of the IL-11/gp130/IL-11 tertiary complex, are within the scope of the present invention. Although the specific examples relate to the use of human-derived IL-11R sequences, the corresponding sequences from other mammals will also work.

The soluble IL-11Rs of the present invention are preferably mutated at one or more of positions 282, 283, 286, 289 and 291, as depicted in SEQ ID NO. 4, all of which are within the gp130 binding site of native IL-11R. Specific preferred mutations are D282 to G, A283 to D, G286 to D, H289 to Y, and V291 to L, independently or in combination of two or more such mutations. Amino acids are described herein with reference to their standard three letter and one letter codes. In particular, the symbols D, G, A, H, Y, V and L have the usual meanings in connection with individual amino acids, namely D represents aspartic acid, G represents glycine, A represents alanine, H represents histidine, Y represents tyrosine, V represents valine and L represents leucine.

Figure 1A:
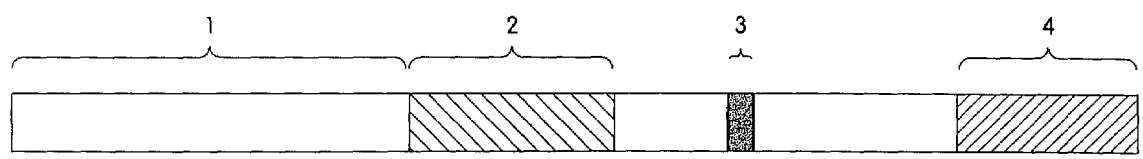
FIG. 1A is a diagrammatic representation of native IL-11 receptor, showing the various regions thereof and its binding interactions with IL-11 and gp130.

Native IL-11R is a known protein having a molecular mass of about 46 kd. Its amino acid sequence has been determined. It comprises several distinct functional regions, as generally illustrated in FIG. 1A of the accompanying drawings. It is normally bound to the cell surface membrane. It has a region for binding to IL-11. Another of its regions, from about position 270–300, is its gp130 binding site. These regions are indicated on FIG. 1A wherein 1 represents the amino-terminal region containing 4 positional conserved cysteine residues, 2 represents an IL-11 binding region, 3 represents a gp130 binding region, and 4 represents the transmembrane domain.

The amino acid sequence of the gp130 binding site is shown in FIG. 2. The present invention, in one of its preferred embodiments, provides IL-11Rs which are mutated in the gp130 binding site illustrated in FIG. 2, by replacement of one or more of the native amino acids in this region with other amino acids. Specific preferred products of the present invention are those which have mutations at one or more of positions 282, 283, 286, 289 and 290 as illustrated and as described above. These mutations effectively reduce or even eliminate binding to gp130, but do not materially affect binding to IL-11.

The mutant soluble IL-11Rs (sIL-11Rs) of the present invention can be prepared by known techniques. In a preferred process, cDNA encoding the IL-11R is cloned by RT-PCR using IL-11R specific primers and total RNA isolated from human osteosarcoma cells. The primers contain terminal restriction endonuclease sites for subsequent cloning into plasmid vectors. The sequence of a preferred cDNA sequence for insertion is depicted in FIG. 1 B. After ligation into a suitable vector, the IL-11R DNA may be expressed in mammalian cells. Baby hamster kidney (BHK) cells constitute an example of a suitable host mammalian cell for this purpose. After extraction and purification, the sIL-11R DNA can be subjected to site-directed mutagenesis to modify the amino acids in the IL-11 receptor which mediate gp130 binding but do not significantly affect IL-11 binding, for example the amino acids identified above.

A second group of preferred compounds in accordance with the present invention are IL-11 binding peptides, which are peptide sequences which selectively interact with IL-11 and prevent the interaction between IL-11 and IL-11R necessary for the formation of the IL-11/IL-11R/gp130 tertiary complex. Surprisingly, it has been determined that small amino acid sequences are capable of binding to IL-11 and preventing the normal interaction between IL-11 and IL-11R. In particular, a peptide with the amino acid sequence Arg Arg Leu Arg Ala Ser Trp Thr Tyr Pro Ala Ser Trp Pro Cys Gln Pro His Phe Leu (SEQ ID NO 1) has been identified which binds IL-11 and prevents its productive interaction with IL-11R. Even more surprisingly, it has been found that the peptide sequence Arg Arg Leu Arg Ala Ser Trp (SEQ ID NO 5) contained in the amino terminus of SEQ ID NO 1 is important to the ability of this peptide to prevent the productive interaction of IL-11 and IL-11R. This short peptide (SEQ ID NO. 5) is also capable of inhibiting the productive interaction of IL-11 and IL-11R. In addition, a third peptide (SEQ. ID. NO. 6) which is located near, but does not overlap, the sequences corresponding to SEQ. ID. NO. 1 or SEQ. ID. NO. 5 on the human IL-11R has been found to inhibit the productive interaction between IL-11 and IL-11R.

Surprisingly, the amino acid sequences of the murine and human IL-11R differ somewhat in the regions corresponding to SEQ. ID. NO 5 and SEQ. ID. NO. 6 (which depict the human sequences). In particular, the human amino acid sequence described in SEQ. ID. NO. 5 is RRLRASW, whereas the murine sequence is RRLHASW (SEQ. ID. NO. 10). Thus, the presence of a basic amino acid residue in the position corresponding to position 4 in peptide 1 (SEQ. ID. NO.5) is preserved between the human and murine sequences, although the actual amino acid in that position varies. Thus, the peptides corresponding to SEQ ID NO 5 and SEQ ID NO 6 are IL-11 binding peptides and peptides having the amino acid sequence RRLXASW, where X is a basic amino acid (SEQ. ID. NO.7) are potential IL-11 binding peptides.

Additionally, SEQ ID NO. 6 depicts the amino acid sequence of an IL-11 binding region identified within the human IL-11R, namely: Ser Ile Leu Arg Pro Asp Pro Pro Gln Gly Leu Arg Val Glu Ser Val Pro Gly Tyr Pro. The corresponding murine sequence is depicted in SEQ ID NO. 8 and is: Ser Ie Leu Arg Pro Asp Pro Pro Gln Gly Leu Arg Val Glu Ser Val Pro Ser Tyr Pro. These sequences differ in their eighteenth amino acid whereby the human peptide has Gly and the murine sequence has Ser. Gly and Ser are both relatively small amino acid residues, having volumes of 60.1 and 89.0 $Å^3$ respectively, and accessible surface areas of 75 and 115 $Å^2$ respectively. This suggests that the relative small size of amino acid 18 in this peptide facilitates interactions with IL-11. However, Gly and Ser differ in their hydrophilicity, suggesting that several factors may interact to govern the suitability of particular amino acid substitutions at position 18 in these peptides. Thus, although IL-11 binding peptides exist which have the amino acid sequence: Ser Ile Leu Arg Pro Asp Pro Pro Gln Gly Leu Arg Val Glu Ser Val Pro xxx Tyr Pro (SEQ ID No. 9), where xxx is a suitable amino acid, it will be necessary to screen potential IL-11 binding peptides having this sequence using the TRAP assay and/or the bone nodule formation assay in order to determine if they are IL-11 binding peptides.

In addition to the amino acid substitutions discussed above, amino acid sequences from other mammals which correspond to IL-11 binding peptides identified from mammalian materials will also be potential IL-11 binding peptides. Thus, where there is variation between mammalian sequences, having identified an IL-11 binding peptide sequence in one mammalian species, it is possible to identify other IL-11 binding peptides with reference to the corresponding amino acid sequences in other mammals, and the pattern of conserved residues observed.

In light of the disclosure of the present application, it is within the capacity of a competent technician to identify and produce peptides capable of interacting with IL-11 and inhibiting the productive interaction between IL-11 and IL-11R, thereby inhibiting or preventing the formation of the IL-11/IL-11R/gp130 complex. It will be obvious to one skilled in the art that peptide sequences containing amino acid substitutions or modifications which preserve the features essential for binding between the peptide and IL-11 are possible and are within the scope of the invention. Such peptides may comprise all or a portion of the amino acid sequence of SEQ ID NO 1, SEQ ID NO 5, SEQ. ID. NO. 6, SEQ. ID. NO.7, SEQ. ID. NO 8, or SEQ. ID. NO. 10. Alternatively, these peptides may have a substantially different amino acid sequence from these sequences, but may have functional attributes permitting specific interactions between these peptides and IL-11. Peptides which are IL-11 binding peptides may be readily identified using one or both of the TRAP assay and the bone nodule formation assay, discussed herein.

Protein and peptide sequences which selectively interact with IL-11 are valuable in vitro as well as in vivo. The present invention teaches a peptide sequence which selectively binds IL-11. It is therefore well within the capacity of a technician of ordinary skill to attach this peptide to a suitable substrate by way of an appropriate linking moiety. Once attached, the immobilized peptide sequence may be used to remove IL-11 from solutions. In particular, immobilized peptides can be used to deplete solutions of IL-11. Alternatively, immobilized peptide can be used to bind IL-11 in one solution, and then release IL-11 in the presence of a second solution, thereby allowing the production of a solution enriched in IL-11 or with a reduced number or quantity of components other than IL-11.

Thus, another preferred embodiment of the present invention is a process of selectively removing IL-11 from solutions using immobilized peptides of the invention having an affinity for IL-11.

In this application, the term "small molecule" refers to a compound having a molecular weight of no more than 30 kd, and the term "IL-11 antagonist" refers to compounds which inhibit or prevent the productive interaction between IL-11 and IL-11R and which are less effective than IL-11 at promoting the productive interaction of IL-11R and gp130.

Particular IL-11 antagonists useful in the treatment of IL-11 related bone density disorders may be identified using the TRAP assay and the bone nodule formation assay, discussed herein. The TRAP assay is known in the art and involves co-culturing murine calvaria (osteoblasts) and bone marrow cells in vitro and then quantifying osteoclast formation by counting the number of tartrate-resistant acid phosphatase positive (TRAP+) multinucleated cells. In light of the disclosure herein, and particularly the information pertaining to IL-11 binding peptides, including their sequences and the pattern of conserved residues, it is within the capacity of a competent technician to design potential IL-11 antagonists which are not peptides but which have comparable binding specificities. These potential IL-11 antagonists may be screened to determine if they are IL-11 antagonists by examining their activity in the TRAP assay and the bone nodule formation assay.

Other preferred embodiments of the present invention are the use of the TRAP assay and the bone nodule formation assay, individually or in combination, to screen samples for the presence of IL-11 antagonists, and to identify IL-11 antagonists.

A third group of preferred compounds are peptides which bind to IL-11R and prevent its productive interaction with IL-11. Candidate peptides which bind to IL-11R can be designed by molecular modelling of the IL-11/IL-11R binding site in light of the disclosure in the present application. Alternatively, such peptides can be identified by screening potential peptides. IL-11R binding peptides may be identified from potential peptides by the ability of IL-11R binding peptides to reduce the formation of TRAP+ MNC's in the TRAP assay and/or the ability of IL-11 binding peptides to reduce the inhibitory effect of IL-11 on bone nodule formation in vitro, using the bone nodule formation assay.

A fourth type of preferred compound for use in the present invention for inhibiting or preventing the formation of the IL-11/IL-11R/gp130 tertiary complex comprises antibodies which selectively bind to one of the components of the complex to interfere with the interaction between components to form the tertiary complex. Some anti-IL-11 antibodies are commercially available. Alternatively, antibodies may be prepared using standard techniques following the injection of a compound comprising the peptide of interest into a suitable animal. Useful antibodies include anti-IL-11 antibodies, anti gp130 antibodies, anti-IL-11R antibodies, and humanized monoclonal antibodies specific for a site of interest on one of the components of the tertiary complex.

The current invention teaches the sequence of the human IL-11R protein, the sequence of several IL-11 binding peptides, the sequence of IL-11 binding regions on the human and murine IL-11Rs, and the sequence of the gp130 binding region on IL-11R, as well as the means for the production of soluble IL-11Rs. It is, therefore, within the capability of a competent technician to produce and screen antibodies which specifically bind either the IL-11 binding region or the gp130 binding region on the IL-11R. These specific antibodies may be used to specifically inhibit the binding of IL-11 to the IL-11R through this binding region, thereby inhibiting formation of the aforementioned complex in vivo without substantially affecting the levels of IL-11 in solution. This may be particularly useful in situations where it is desired to inhibit the formation of the IL-11/IL-11R/gp130 complex, but it is still desired to maintain free IL-11 and functional gp130 to achieve some other biological effect.

A fifth type of preferred compound for use in the present invention for inhibiting or preventing the formation of the IL-11/IL-11R/gp130 tertiary complex comprises small molecules capable of interfering with the IL-11R/IL-11 interaction by specific binding to either IL-11 or IL-11R in the IL-11/IL-11R binding region. Small molecule antagonists of IL-11 and IL-11R may be identified using the TRAP assay and the bone nodule formation assay. Both IL-11 antagonists and IL-11R antagonists may be identified and/or synthesized in light of the features of the binding region of the compounds of the present invention. Features such as size, shape, hydrophilicity and charge which control molecular binding affinity are well understood, and it is well within the capacity of a competent technician to identify candidate small molecules having the potential to bind either IL-11R or IL-11 using molecular modelling in light of the peptides and proteins of the present invention. It is also within the capacity of a competent technician to screen the candidate small molecules for the ability to inhibit or prevent the formation of the IL-11/IL-11R/gp130 complex using the TRAP assay and the bone nodule formation assay, known in the prior art and described below.

In light of the teachings of the present invention, it is also within the capability of a competent technician to produce transcribable genetic material capable of inhibiting the formation of the IL-11/IL-11R/gp130 tertiary complex.

One variety of transcribable genetic material which can be used is DNA encoding antisense RNA complementary to the mRNA encoding a component necessary to the formation of the IL-11/IL-11R/gp130 tertiary complex (including IL-11, IL-11R, gp130, or portions thereof, and capable of inhibiting or preventing the translation of this mRNA. The mRNA sequence of IL- 11 has been previously reported and sequence listings may be founds in the GENBANK database (Accession No.s M57766, M37007 (M. *Fascicularis*), Accession Nos. M81890, M57765, M37006 (human)). The mRNA sequence of gp130 has been previously reported and sequence listings may be founds the GENBANK database (Accession No.s M83336, MX62646). The mRNA sequence of the IL-11R alpha chain has been reported and a sequence listing may be found in the GENBANK database (Accession No. U32324). In light of this sequence information and the disclosure in the present patent application it is within the capacity of a competent technician to produce transcribable genetic material capable of inhibiting the formation of the IL-11/IL-11R/gp130 tertiary complex. The capacity of a particular antisense mRNA to inhibit the translation of a component of the IL-11/IL-11R/gp130 complex may be assessed using standard methods.

Antisense sequences may be used to inhibit the translation of the corresponding protein of interest (including IL-11, IL-11R, and gp130), thereby effecting a reduction in levels of that protein in the treated cells. This reduction of protein levels will reduce the protein available for binding in the IL-11/IL-11R/gp130 tertiary complex, thereby reducing the formation of the tertiary complex. Transcribable genetic material encoding antisense nucleic acid sequences may be introduced into subjects by standard techniques, including gene therapy.

A second type of transcribable genetic material which may be used to inhibit the formation of the IL-11/IL-11R/gp130 tertiary complex is transcribable genetic material encoding amino acid sequences capable of inhibiting the formation of the tertiary complex and containing amino acid sequences targeting these sequences to the appropriate location upon translation. Examples of such amino acid sequences are soluble mutant IL-11Rs, IL-11 binding peptides, and IL-11R binding peptides of the present invention with suitable amino acid residues added which target these sequences for secretion. Protein targeting and selective cleavage sequences are known in the art and it is well within the capacity of a competent technician to produce transcribable genetic material encoding the amino acid sequence of interest and targeted for secretion.

In addition to the amino acid sequences discussed above, it is well within the capacity of a competent technician to identify other amino acid sequences which will inhibit or prevent the formation of the IL-11/IL-11R/gp130 tertiary complex using the TRAP+assay, and/or the bone nodule formation assay. Having identified a peptide or protein which is capable of inhibiting the formation of the tertiary complex, it is possible to determine the amino acid sequence of that peptide or protein using standard methods. It is therefore well within the capacity of a competent technician to devise an expressible genetic element encoding the amino acid sequence of the peptide or protein of interest and bearing the desired post-translational modification and targeting information.

Transcriptional regulation elements may be selected so that the transcribable genetic material of the present invention is constitutively transcribed. Alternatively, the level of transcription may be regulated by transcriptional control elements which are sensitive to the level of an inducing compound. Suitable inducing compounds include substances naturally produced by tissues in the patient's body, the level of which may vary with the disease state or other factors. Alternately, the inducing compound may be a substance which is not normally present in levels sufficient to allow transcription of the transcribable genetic material. In such a case, the inducing compound may be introduced into the subject at the time and dosage necessary to stimulate the desired level of transcription.

Post menopausal osteoporosis is characterized by a general reduction in bone mass, resulting from an imbalance between osteoblast-mediated bone formation and bone resorption by the osteoclast. While the osteoblast is responsible for the formation of new bone or osteoid, it also appears to control the activation and/or number of osteoclasts by releasing cytokines such as IL-6 or IL-11. This process can be examined using a "TRAP assay" which involves co-culturing murine calvaria (osteoblasts) and bone marrow cells in vitro and then quantifying osteoclast formation by counting the number of tartrate-resistant acid phosphatase positive (TRAP+) multinucleated cells. Ovariectomized (OVX) rats or mice provide a satisfactory animal model for postmenopausal women in studies of osteoporosis.

Initial experiments comparing the ability of marrow cells isolated from sham-operated, OVX, and OVX mice treated with IL-11 neutralizing antibody, to form osteoclasts in vitro demonstrated that IL-11 Ab treatment reduces osteoclast levels below those obtained from sham-operated animals. Accordingly, since bone density is determined by balancing bone formation with bone resorption, inhibitors of IL-11R binding to gp130 reverse bone loss in post-menopausal patients.

Using cocultures of murine calvaria and bone marrow cells, it has been shown that IL-11 is a potent simulator of osteoclast formation in vitro. Moreover, it has been demonstrated that IL-11 inhibits bone formation when murine calvaria cells (primary osteoblasts) are cultured in the presence of 250 $\mu$M ascorbic acid and 10 mM $\beta$-glycerol phosphate (the "bone nodule formation assay"). Thus, by targeting IL-11 one can not only inhibit the process of osteoclastogenesis and therefore pathological bone loss, but one can also restore previously lost bone by stimulating the process of bone formation.

The in vitro TRAP assay also provides a convenient means to screen the effectiveness of soluble mutant IL-11Rs, IL-11-binding peptides, IL-11R binding peptides, and small molecules prior to use in vivo. In particular, when small molecules, IL-11 binding peptides, IL-11R binding peptides or mutant IL-11Rs are produced, their effectiveness at inhibiting the formation of a functional tertiary complex may be assessed in vitro using the TRAP assay. Those compounds causing a significant reduction in TRAP+ MNC's in the presence of exogenous IL-11 under assay conditions are deemed to be effective at inhibiting the formation of the tertiary complex. Where a potential compound of interest is contained within a mixture of compounds, it may be desirable to separate these compounds by standard means prior to examination using the TRAP assay. Such separation will allow the removal of potentially undesirable compounds, as well as reducing the number of possible compounds producing the results observed.

In addition to allowing the identification of compounds useful to inhibit the formation of the tertiary complex, the TRAP assay allows an assessment of the relative effectiveness of various compounds of the present invention. The terms small molecule, IL-11 binding peptide, IL-11R binding peptide and mutant IL-11R when used herein refer to small molecules, peptides or proteins which are effective at inhibiting the formation of the IL-11/IL-11R/gp130 tertiary complex in vitro when tested using the TRAP+ assay. The terms anti IL-11 antibody, and anti IL-11R antibody when used herein refer to antibodies or portions or functional equivalents thereof which are effective at inhibiting the formation of the IL-11/IL-11R/gp130 tertiary complex in vitro when tested using the TRAP assay.

The bone nodule formation assay provides a second convenient method to screen the effectiveness of soluble IL-11R's, IL-11 bonding peptides, IL-11R binding peptides, and small molecules at inhibiting the formation of the IL-1/IL-11R/gp130 tertiary complex. A compound to be assessed may be added to the bone nodule formation assay system, and the effect of the compound on bone nodule formation may be assessed. As with the TRAP assay, in some circumstances it may be desirable to separate various compounds contained within a sample prior to examination using the bone nodule formation assay. Those compounds causing a significant reduction in the inhibition of bone nodule formation by IL-11 under assay conditions are deemed to be effective at inhibiting the formation of the tertiary complex. In addition to allowing the identification of compounds useful in inhibiting the formation of the tertiary complex, this assay allows an assessment of the relative effectiveness of various compounds of the present invention.

Compounds of the present invention may be administered systemically or locally, by various modes of administration, and in various forms. One form in which the proteins, peptides, and small molecules of the invention may be administered is in liquid form, as solutions or suspensions in appropriate, biologically acceptable carriers. A preferred means of delivering such liquid compounds is by injection. Alternately, the proteins, peptides, and small molecules of the present invention may be encapsulated for oral administration. The encapsulation material may be selected to allow the release of the encapsulated compounds at an optimal stage in the digestive process to allow maximal biological effect.

Where localized treatment is desired, the compounds of the present invention may be included in a suitable matrix for implantation near the desired treatment site. Such matrices may be permanent or biodegradable, depending on the clinical needs of the patient. One particularly effective means of localized administration is the inclusion of compounds of the present invention in implanted pins used in the immobilization of bone fractures. Another preferred form of local administration is by injection into the region of the mammalian patient's body proximate to the site affected by the disorder under treatment.

The transcribable genetic material of the present invention may be administered systemically or locally, by various modes of administration. Where it is desired to use antisense RNA sequences to inhibit translation of a cellular protein, the DNA encoding the antisense RNA may introduced into the nuclei of target cells by standard means. Where it is desired to introduce DNA sequences encoding protein or peptide products capable of inhibiting the formation of the IL-11/IL-11R/gp130 tertiary complex, the DNA may be introduced into the nuclei of cells already present in the patient's body by standard means. Alternatively, the DNA may be introduced into the nuclei of MHC-compatible cells by standard means in vitro, and the resulting cells expressing the introduced DNA may be administered to the patient systemically or locally by standard means such as intravenous injection, or local injection near sites of concern.

The desired dosage of active compound will vary, depending on the mode of administration, the condition to be treated, the overall condition of the subject, and the compound administered. It is well within the capability of a competent technician to determine the appropriate dosage for a particular patient in light of these factors. It is anticipated that where the systemic administration of the solubilized mutant IL-11R of the present invention by injection is desired, the appropriate dosage will be between 1 mg to 20 mg of the soluble mutant IL-11R per kg body weight. Depending on the subject and the condition to be treated, dosages will be more preferably between 1 to 10 mg per kg body weight for subjects whose existing bone density is not extremely low and between 10 mg to 20 mg per kg body weight for subjects whose bone density is extremely low. It is anticipated that in many pathological conditions the appropriate systemic dosage of solubilized mutant IL-11R will be similar to the appropriate dosage of parathyroid hormone for the treatment of a comparable patient.

Where localized administration of the compounds of the present invention is desired, the appropriate localized dosage can be determined with reference to the level of compound desired in the treatment area. It is anticipated that the total dosage required for localized treatment will be lower than that level required for systemic treatment, and in many cases the appropriate localized dosage will be ten to one-hundred fold lower than the amount of compound required for systemic treatment.

Where it is desired to use a small molecule, IL-11 binding peptide, IL-11R binding peptide or a specific antibody instead of, or in addition to, solubilized mutant IL-11R, the appropriate dosage may be easily determined based on the appropriate dosage of IL-11R. The small molecule, peptide or antibody dosage will be a function of the solubilized mutant IL-11R dosage, adjusted to provide a comparable level of effective target binding based on the abundance of the target, the relative molecular mass and binding affinity of the small molecule, peptide or antibody for its target relative to the solubilized mutant IL-11R, its relative effectiveness at blocking tertiary complex formation in vitro, and its relative half-life in vivo. Target abundance, molecular mass, binding affinity and in vivo half life of a particular small molecule, antibody or peptide may be determined by standard methods. The effectiveness of the compound at blocking the formation of the tertiary complex in vitro may be assessed using the TRAP assay and/or the bone nodule formation assay, as previously discussed. It is anticipated that the appropriate dosage of the IL-11-binding peptides of the present invention when administered by local injection will frequently be between 0.1 to 10 mg per kg body weight. The dosage of a particular IL-11 binding peptide needed for a particular patient may be easily determined with reference to the factors discussed above, the patient's overall condition, and the disorder to be treated.

In some instances it will be desirable to enhance the activity and/or in vivo half-life of the peptides of the present invention by the chemical modification of these peptides to increase activity or to inhibit in vivo degradation. For example, chemical moieties may be covalently attached to specific amino acids to interfere with the action of degradative enzymes. Alternatively or additionally, specific amino acids in the peptide sequence may be chemically modified to increase the overall peptide half life without greatly reducing specific binding between the peptide and IL-11. Additionally, it will be desirable in some instances to employ one or more D-isomer amino acid residues in the formation of these peptides. In some instances it will be desirable to cyclize the peptides. For example, cyclization can be used to stabilize a particular peptide conformation in order to obtain a desired level of binding. Methods of modifying peptide sequences by the addition of chemical moieties to amino acids, the chemical modification of specific amino acids, the cyclization of peptides, and the incorporation of D-isomers of amino acids are known in the art and it is within the capacity of a competent technician in light of this disclosure to determine what modifications are appropriate and how to effect these modifications.

Where the compound to be administered comprises antisense genetic material to be expressed within the patient's cells, the appropriate dose will also depend on the level of transcription of the antisense material, and its stability and binding affinity for its complementary IL-11R RNA in the cell.

Alternatively or additionally, expressible genetic material encoding a secreted form of a protein or peptide sequence of interest may be introduced into suitable MHC-compatible cells ex vivo by standard methods and these cells may be introduced into the body of the patient by standard methods. These cells may be administered locally in the region where increased bone deposition or decreased bone resorption is needed, or they may be administered generally. The expressible genetic element may be constitutively active, or it may be inducible. The appropriate dosage of expressible genetic elements will depend on the mode of administration, the condition to be treated, the patient's condition, the stability of the coding RNA and its protein product, the level of protein expression, and other factors influencing the level of effective target binding, as discussed in relation to IL-11 binding peptides, IL-11R binding peptides, small molecules and specific antibodies. In general, it is anticipated that the appropriate dosage of expressible genetic elements will be the dosage which leads to a level of secreted protein or peptide in the vicinity of the target cells which is generally similar to the level of protein or peptide present in the vicinity of the target cells when the appropriate level of that peptide is administered directly to the patient.

Where the compound to be administered comprises an antibody which specifically binds to IL-11, IL-11R, or gp130 and prevents or inhibits the formation of the tertiary complex, either systemic or localized administration of the compound may be possible. Localized administration may be accomplished by various means, including the injection of a solution containing the antibody of interest into the region proximate to the tissue to be treated. Alternatively or additionally, MHC-compatible cells secreting the antibody of interest may be introduced into the subject's body in either a systemic or a localized manner.

The invention is further described, for illustrative purposes, in the following specific examples.

EXAMPLE 1

IL-11 Inhibits Bone Nodule Formation

The effect of IL-11 on bone formation was examined using the bone nodule formation assay. Murine calvaria cells (primary osteoblasts) were cultured in the presence of 250 $\mu$M ascorbic acid and 10 mM $\beta$-glycerol phosphate, and in the presence of various amounts of interleukin-11. After culturing, the culture media were plated out and the number of bone nodules per plate was counted.

Figure 5:
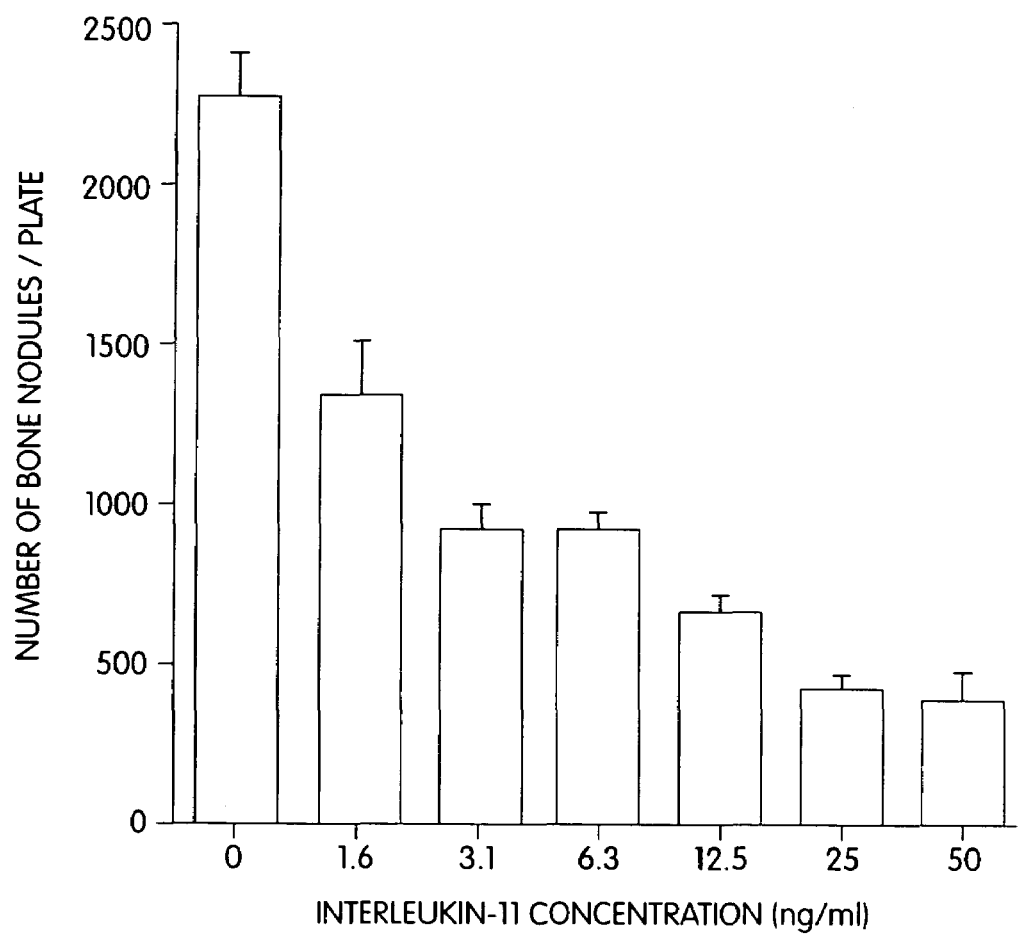
FIG. 5 is a graphical presentation of the results obtained according to Example 1 below.

The results are shown on the accompanying FIG. 5, where number of bone nodules per plate is plotted as the vertical axis, with the different concentrations of interleukin on the horizontal axis, not to scale. Each bar represents the result on experiments containing a different concentration of interleukin-11, as noted on FIG. 5.

It is clearly seen that the experiment conducted in the absence of interleukin-11 led to the highest number of bone nodules per plate, and that the number of bone nodules per plate decreased as the interleukin-11 concentration increased. This demonstrates that IL-11 inhibits bone formation.

EXAMPLE 2

Demonstration of the Ability of Anti-IL-11-Neutralizing Antibodies to Halt and to Reverse Bone Loss in Ovariectomized Animals Twenty four laboratory mice were divided into four equal groups of six. Three of the groups were ovariectomized (OVX) while the fourth group was sham-operated (SHAM), to act as a control. One week after ovariectomization, treatment of one group of ovariectomized animals (OVX+Anti IL-11 Ab) with a daily dose of 160 $\mu$g/mouse of anti-IL-11 Ab (an affinity-purified sheep anti-murine IL-11 polyclonal neutralizing antibody) commenced. At the same time, treatment of another group of ovariectomized animals (OVX+NSIgG) with the same daily dosage of normal sheep immunoglobulin (NSIgG) was commenced. Treatments were delivered once daily by intraperitoneal injection. Plasma analysis demonstrated that IgG entered the circulation of NSIgG group animals. Animals in the remaining two groups received no treatment.

On the day on which treatment was commenced, the sham-operated animals (Sham-Baseline) and an equal number of the untreated ovariectomized animals (OVX-Baseline) were sacrificed to obtain their right femurs for histomorphometric analysis, so that baseline values could be established.

On day 21 after the commencement of the treatment, the remaining animals were similarly killed and their right femurs removed for bone histomorphometry. For this, the undecalcified distal third of the right femur of each mouse was embedded in glycolmethacrylate (JB-4 embedding medium; Analychem, Toronto, Ontario, Canada). Histologic sections of 6 to 8 $\mu$m were obtained using a Riechert Jung microtome (model K4; Riechert Jung Canada, Toronto, Ontario), mounted, and then stained with either 1% toluidine blue or hematoxyline and eosin (H & E) before being subjected to morphometric analysis. In each case, a region 800 $\mu$m below the epiphyseal growth plate that included the entire metaphysis was subjected to light microscopy using a Merz grid (Carl Zeiss Canada, Don Mills, Ontario). Sections examined in this fashion encompassed a total tissue area of 5–8 mm$^2$. The following parameters were determined: (1) cancellous bone volume, (2) osteoblast surface, (3) osteoid surface, and (4) osteoclast surface. For each section, cancellous bone volume was calculated from a total of >1,600 point measurements (45 fields; 400× magnification), which were selected at random using the Merz grid. The percent osteoblast, osteoid, or osteoclast surface was calculated under oil immersion (1,000×) by recording the presence or absence of each where the hemispherical grid of the Merz radical crossed cancellous bone. Osteoblasts were identified morphologically as distinct cuboidal-shaped cells lining the cancellous bone surface, whereas osteoclasts were identified morphologically as large multinucleated cells in close proximity to the cancellous bone surface, which stained for tartrate-resistant acid phosphatase (Sigma Chemical Co., St. Louis, Mo.; Procedure No. 386).

The results of measurements of cancellous bone volume are presented graphically in FIG. 6A. Clearly the animals of the OVX+Anti IL-11 Ab group, treated with IL-11 antibody, had a much larger volume of cancellous bone than the untreated OVX group and the negative control OVX NSIgG, IgG treated group. Measurements on the femurs from sham and OVX animals sacrificed on the day on which treatment was commenced establish baseline values for the bone volume increases. It will be noted that the test animals of the OVX+Anti IL-11 Ab group showed a significant gain in cancellous bone volume as compared to OVX baseline, indicating that cancellous bone loss was not only prevented but that it was reversed by the inhibition of biological activity of IL-11.

FIG. 6 B of the accompanying drawings presents the results of osteoid surface measurements, and indicates that the OVX+Anti IL-11 Ab animals exhibited higher rates of bone formation than the comparative groups, demonstrating that by inhibiting IL-11 biological activity one can promote the formation of new bone, reverse bone loss, and increase bone density in OVX mice.

FIG. 6 C of the accompanying drawings similarly presents the results of osteoclast surface measurements, and shows a notable reduction in the case of the OVX+Anti IL-11 Ab animals treated with the IL-11 antibodies. This again indicates that the OVX+Anti IL-11 Ab animals exhibited much less bone resorption than the comparative groups, in further demonstration of the fact that inhibition of biological activity of IL-11 prevents and even reverses bone resorption in OVX mice.

EXAMPLE 3

Preparation of Soluble Interleukin-11Receptor that Inhibits IL-11 Induced Osteoclast Formation cDNA encoding the IL-11 receptor (minus the transmembrane and cytoplasmic domains) was cloned by RT-PCR using IL-11 receptor specific primers and total RNA isolated from the human osteosarcoma cell line SAOS-2. Primer sequences were based on the DNA sequence for the human IL-11 receptor α-chain. The forward primer contains a Kozak consensus sequence preceding the start ATG codon, while the reverse primer contains, in addition to a termination codon, bases encoding a histidine tag. Both primers contain terminal restriction endonuclease sites for subsequent cloning into plasmid vectors. Authenticity of the cDNA insert encoding the soluble IL-11 receptor (cDNA depicted in SEQ ID NO 3) is confirmed by restriction endonuclease analysis and by double-stranded DNA sequencing using a modified T7 DNA polymerase system (Sequenase, Amersham).

For stable expression in mammalian cells, the IL-11R cDNA is gel-purified and ligated into the pcDNA3.1 vector (Invitrogen, Carlsbad, Calif.) which encodes a neomycin gene and allows for selection under high concentrations of G418. The cDNA is inserted upstream of the human cytomegalovirus (CMV) immediate-early promoter/enhancer (this allows for high-level expression in a variety of mammalian cell lines) and downstream of the bovine growth hormone (BGH) polyadenylation signal (which allows for efficient transcript stabilization and termination). The cDNA sequence to be inserted was formed from the cDNA sequence corresponding to nucleotides 62 to 1156 on the IL-11R cDNA as identified by Van Leuven et al., with an additional 39 nucleotides added to the 3' end of this sequence to provide a thrombin cleavage site, a histidine tag, and a stop codon. The cDNA sequence inserted (SEQ ID NO. 3) is depicted in FIG. 1B.

Proper orientation of the inserted IL-11R cDNA is confirmed by using restriction endonuclease analysis and DNA sequence analysis. After approximately 10–12 days of selection in medium containing neomycin, drug-resistant colonies are isolated and the highest secreting clones are seeded into roller bottles and the medium collected every 2–3 days. Soluble IL-11R is purified from the collected medium using a $Ni^{2+}$-IDA column and subsequently eluted using EDTA. Antigen levels are determined by ELISA using antibodies to both the histidine tag as well as the IL-11 receptor.

To assure that the sIL-11R does not associate with gp130, site-directed mutagenesis is used to modify the amino acids in the IL-11 receptor which mediate gp130 binding but do not affect IL-11 binding. Specifically, the process mutates D282 to G, A283 to D, G286 to D, H289 to Y, and V290 to L, independently or in combination. The relevant portion of the IL-11R, and the preferred mutations, are depicted in FIG. 2. Site-directed mutagenesis is performed as described previously (Austin, Richard C. et al. "FEBS Letters", Vol. 280, No. 2, 254:258 (March 1991) Federation of European Biochemical Societies) using mutant oligodeoxynucleotide primers synthesized at the Central Facility of the Institute for Molecular Biology and Biotechnology, McMaster University. Prior to expression in BHK cells, the resultant sIL-11R mutant cDNAs are then inserted into pcDNA3.1, and the sequences of all the sIL-11R mutant cDNAs are confirmed by sequencing as described above.

EXAMPLE 4

Determination of the Effect of a sIL-11R Antagonist on IL-11 Induced Osteoclast Formation In Vitro The effect of IL-11 on osteoclast development in cocultures of murine bone marrow and calvaria cells was examined using standard techniques. Briefly, bone marrow cultures were established by removing femurs from mice, dissecting away soft tissue, and removing the distal and proximal ends of the femur. The marrow was then flushed with 5 ml α MEM and 1.0% penicillin-streptomycin using a 25 gauge needle. The bone marrow cells were then suspended to a concentration of 5 000 000 cells per ml in α MEM containing 15% fetal calf serum (charcoal treated) to remove cells adherent to plastic. The non-adherent cells were then co-cultured for an additional 9 days with murine calvaria cells prior to being fixed and stained for TRAPase activity (stains were obtained from Sigma Chemical Co., St. Louis, Mo.). TRAP+ MNC's have the ability to form resorption pits in smooth cortical bone slices and are therefore considered to be of osteoclast origin.

(i) IL-11 Dose-Dependancy of TRAP+ Cell Formation

The effect of IL-11 on osteoclast development in cocultures of murine bone marrow and calvaria cells was examined by maintaining these cultures in the presence of various specific concentrations of IL-11 for 9 days. After 9 days of culture, the cells were stained for TRAPase activity and the number of multinucleated TRAP+ cells were determined. The results of this experiment are depicted in Table I. Data are expressed as mean +/− SEM.

(ii) Impact of Mutant IL-11Receptor on IL-11 Induced Osteoclast Formation

In order to assess the effect of a gp130 binding region mutant IL-11R on IL-11 induced osteoclast formation, the procedure described in (i) above was repeated using 20 ng/ml IL-11 and 10, 100, or 1000 ng/ml of either (A) the H289→Y289 mutant solubilized IL-11 receptor described in Example 3, or (B) a corresponding solubilized native IL-11 receptor. The results of this experiment, depicted in FIGS. 7 A and B, demonstrate that a mutant IL-11 receptor is capable of inhibiting IL-11-induced osteoclast formation, whereas the native IL-11 receptor is not.

EXAMPLE 5

Determination of the Effect of a Peptide IL-11R Antagonist on IL-11 Induced Osteoclast Formation In Vitro It is desirable to have a means of selectively inhibiting the interaction of IL-11 with the IL-11R, without adding exogenous antibodies or other large proteins. Surprisingly, it was determined that a short peptide sequence could be created which is capable of inhibiting the interaction between IL-11 and the IL-11R. A peptide with the amino acid sequence Arg Arg Leu Arg Ala Ser Trp Thr Tyr Pro Ala Ser Trp Pro Cys Gln Pro His Phe Leu ("peptide 1", SEQ ID NO. 1) was synthesized which is homologous to a region in the IL-11 receptor which appears to bind IL-11.

To determine if peptide 1 could inhibit IL-11-induced MNC formation, the procedure of Experiment 4 was repeated using peptide 1 in place of the gp130 binding region mutant IL-11 receptor protein, and using an overlapping peptide ("peptide 2", SEQ ID NO. 2) in place of the solubilized native IL-11 receptor. Peptide 2 has the amino acid sequence Thr Tyr Pro Ala Ser Trp Pro Cys Gln Pro His Phe Leu Leu Lys Phe Arg Leu Gln Tyr (SEQ ID NO 2) and represents a portion of the amino acid sequence occurring in the native IL-11 receptor, and overlapping in part with the sequence of peptide 1. Peptide 2 lacks the N-terminal Arg Arg Leu Arg Ala Ser Trp sequence (SEQ ID NO. 5) which is contained in peptide 1. The sequence of these peptides is depicted in FIG. 4.

Peptide 1 inhibits IL-11 induced osteoclast formation, whereas peptide 2 does not. The results of this experiment pertaining to peptide 1 are depicted in FIG. 8. This indicates that a peptide sequence comprising Arg Arg Leu Arg Ala Ser Trp is capable of interacting with IL-11 and acting as an antagonist to IL-11 mediated activation of the osteoclast formation. The ability of peptide 1, and particularly the peptide sequence Arg Arg Leu Arg Ala Ser Trp to inhibit osteoclast formation indicates that this peptide is interacting with IL-11. Thus, peptide 1 is an example of an IL-11 binding peptide.

EXAMPLE 6

Determination of the Effect of IL-11 Antagonists on the Ability of IL-11 to Inhibit Bone Nodule Formation In Vitro It was desired to determine if the IL-11 antagonists of the invention could control bone nodule formation, and in particular, if these antagonists could reduce the inhibitory effect of IL-11 on bone nodule formation.

Bone nodule formation was measured using standard techniques. Briefly, calvaria cell cultures were established as follows: Calvaria cells were obtained from 2 day old fetal mouse calavariae by collagenase digestion. The cells were then cultured for 21 days in the presence of 0.5 mM ascorbic acid and 10 mM β-glycerophosphate. Where indicated in the experimental descriptions below, IL-11 and the mutant IL-11 receptor of experiment 4 were added to the culture at day 0 and every 3–4 days thereafter until the removal of the medium for analysis. Bone nodule formation was quantified by counting alizarin red stain nodules under a light microscope.

Exogenous IL-11 alone added to murine calvaria cell culture can inhibit bone nodule formation, as depicted in FIG. 5. The effect of a gp130 binding region mutant soluble IL-11 receptor of type described in Experiment 4 and produced by the process of Experiment 3 on bone nodule formation in the presence of 20 ng/ml of exogenous IL-11 was assessed, and the results are depicted in FIG. 9. These results indicate that very low levels of mutant solubilized IL-11 receptor can reverse the effect of exogenous IL-11. Moreover, the addition of 10 ng/ml of the mutant receptor used in this experiment was capable of allowing enhanced bone nodule formation relative to the level observed in the absence of exogenous IL-11. Thus, IL-11 antagonists such as mutant IL-11Rs can enhance bone nodule formation.

EXAMPLE 7

Determination of the Effect of an IL-11 Antagonist Peptide on the Ability of IL-11 to Inhibit Bone Nodule Formation In Vitro It was desired to determine if bone nodule formation could be modulated in a manner similar to that reported in Example 6 using an IL-11 antagonist peptide such as the one used in Example 5. To achieve this, the procedure of Example 6 was repeated, with the substitution of peptide 1 for the solubilized mutant IL-11 receptor. The results of this experiment are depicted in FIG. 10. Peptide 1 was able to reduce the inhibitory effects of 20 ng/ml exogenous IL-11 at very low concentrations, and at concentrations of 50 ng/ml, peptide 1 allowed bone nodule formation in excess of that seen in the control samples. Peptide 2 was unable to reduce the inhibition of nodule formation by IL-11. Thus, peptide 1 (SEQ ID NO. 1), and particularly the peptide sequence Arg Arg Leu Arg Ala Ser Trp (SEQ ID NO.5), is capable of allowing enhanced bone nodule formation.

What is claimed is:

1. A method for the treatment of a clinical condition comprising increased bone resorption or decreased bone formation, the method comprising administering to said patient an effective amount of an anti-IL-11 antibody, which inhibits the formation of a tertiary complex of Interleukin-11 (IL-11), Interleukin-11 receptor (IL-11R), and glycoprotein 130 (gp130), to increase osteoblast-mediated bone formation and to decrease osteoclast-mediated bone resorption.

2. The method of claim 1, wherein the clinical condition is postmenopausal bone loss.

3. The method of claim 1, wherein said anti-IL-11 antibody is a small molecule no more than 30 kd in molecular weight.

4. The method of claim 1, wherein said anti-IL-11 antibody is a whole antibody of isotype IgG, IgA, IgM, IgD, or IgE, or a functional fragment thereof which retain an antigen binding site.

5. The method of claim 1, wherein said anti-IL-11 antibody is a chimeric, hybrid, or genetically engineered antibody, or a functional fragment thereof which retain an antigen binding site.

6. The method of claim 1, wherein said IL-11 antibody is a proteolytic and/or recombinant fragment, comprising Fab, $F(ab')_2$, Fab', Fv, or single chain antibody (scFv) containing a V[L] and/or V[H] domain joined by a peptide linker.

7. The method of claim 1, wherein said IL-11 antibody comprises several scFv covalently or non-covalently linked to form an antibody having two or more binding sites.

8. The method of claim 1, wherein said IL-11 antibody is a polyclonal antibody.

9. The method of claim 1, wherein said IL-11 antibody is a purified preparation of antibodies or recombinant antibodies.

10. The method of claim 1, wherein said IL-11 antibody is a monoclonal antibody.

11. The method of claim 10, wherein said monoclonal antibody is a humanized monoclonal antibody.

* * * * *

SEQUENCE LISTING

<160> NUMBER OF SEQ ID NOS: 11

<210> SEQ ID NO 1
<211> LENGTH: 20
<212> TYPE: PRT
<213> ORGANISM: Homo sapiens

<400> SEQUENCE: 1

Arg Arg Leu Arg Ala Ser Trp Thr Tyr Pro Ala Ser Trp Pro Cys Gln
 1               5                  10                  15

Pro His Phe Leu
            20

<210> SEQ ID NO 2
<211> LENGTH: 20
<212> TYPE: PRT

<213> ORGANISM: Homo sapiens

<400> SEQUENCE: 2

Thr Tyr Pro Ala Ser Trp Pro Cys Gln Pro His Phe Leu Leu Lys Phe
 1               5                  10                  15

Arg Leu Gln Tyr
            20

<210> SEQ ID NO 3
<211> LENGTH: 1140
<212> TYPE: DNA
<213> ORGANISM: Mus musculus

<400> SEQUENCE: 3

| | | | | | |
|---|---|---|---|---|---|
| atgagcagca | gctgctcagg | gctgaccagg | gtcctggtgg | ccgtggctac | agccctggtg | 60 |
| tcttcctcct | cccccctgccc | ccaagcttgg | ggtcctccag | gggtccagta | tggacaacct | 120 |
| ggcaggcccg | tgatgctgtg | ctgccccgga | gtgagtgctg | ggactccagt | gtcctggttt | 180 |
| cgggatggag | attcaaggct | gctccaggga | cctgactctg | ggttaggaca | caaactggtc | 240 |
| ttggcccagg | tggacagccc | tgatgaaggc | acttatgtct | gccagaccct | ggatggtgta | 300 |
| tcaggggca | tggtgaccct | gaagctgggc | tttcccccag | cacgtcctga | agtctcctgc | 360 |
| caagcggtag | actatgaaaa | cttctcctgt | acttggagtc | caggccaggt | cagcggtttg | 420 |
| cccacccgct | accttacttc | ctacaggaag | aagacgctgc | aggagctga | gagtcagagg | 480 |
| gaaagtccat | ccaccgggcc | ttggccgtgt | ccacaggacc | ctctggaggc | ctcccgatgt | 540 |
| gtggtccatg | gggcagagtt | ctggagtgag | taccggatca | atgtgaccga | ggtgaaccca | 600 |
| ctgggtgcca | gcacgtgcct | actggatgtg | agattacaga | gcatcttgcg | tcctgatcca | 660 |
| ccccaaggac | tgcgggtgga | atccgtacct | agttacccga | gacgcctgca | tgccagctgg | 720 |
| acatacctg | cctcctggcg | tcgccaaccc | cactttctgc | tcaagttccg | gttgcaatac | 780 |
| cgaccagcac | agcatccagc | gtggtccacg | gtggagccca | ttggcttgga | ggaagtgata | 840 |
| acagatgctg | tggctgggct | gccacacgcg | gtacgagtca | gtgccaggga | ctttctggat | 900 |
| gctggcacct | ggagcgcctg | gagcccagag | gcctggggta | ctcctagcac | tggtcccctg | 960 |
| caggatgaga | tacctgattg | gagccaggga | cacggacagc | agctagaggc | agtagtagct | 1020 |
| caggaggaca | gcccggctcc | tgcaaggcct | tccttgcagc | cggacccaag | gccacttgat | 1080 |
| cacagggatc | ccttggagca | actggtgcca | cgcggttctc | accaccacca | ccaccactga | 1140 |

<210> SEQ ID NO 4
<211> LENGTH: 10
<212> TYPE: PRT
<213> ORGANISM: Homo sapiens

<400> SEQUENCE: 4

Gly Asp Val Ala Asp Leu Pro Tyr Ala Leu
 1               5                  10

<210> SEQ ID NO 5
<211> LENGTH: 7
<212> TYPE: PRT
<213> ORGANISM: Homo sapiens

<400> SEQUENCE: 5

Arg Arg Leu Arg Ala Ser Trp
 1               5

```
<210> SEQ ID NO 6
<211> LENGTH: 20
<212> TYPE: PRT
<213> ORGANISM: Homo sapiens

<400> SEQUENCE: 6

Ser Ile Leu Arg Pro Asp Pro Pro Gln Gly Leu Arg Val Glu Ser Val
 1               5                  10                  15

Pro Gly Tyr Pro
            20

<210> SEQ ID NO 7
<211> LENGTH: 7
<212> TYPE: PRT
<213> ORGANISM: Artificial Sequence
<220> FEATURE:
<221> NAME/KEY: SITE
<222> LOCATION: (4)
<223> OTHER INFORMATION: Xaa=basic amino acid
<223> OTHER INFORMATION: Description of Artificial Sequence: IL-11
      binding peptide

<400> SEQUENCE: 7

Arg Arg Leu Xaa Ala Ser Trp
 1               5

<210> SEQ ID NO 8
<211> LENGTH: 20
<212> TYPE: PRT
<213> ORGANISM: Mus musculus

<400> SEQUENCE: 8

Ser Ile Leu Arg Pro Asp Pro Pro Gln Gly Leu Arg Val Glu Ser Val
 1               5                  10                  15

Pro Ser Tyr Pro
            20

<210> SEQ ID NO 9
<211> LENGTH: 22
<212> TYPE: PRT
<213> ORGANISM: Artificial Sequence
<220> FEATURE:
<221> NAME/KEY: SITE
<222> LOCATION: (18)..(20)
<223> OTHER INFORMATION: Xaa=suitable amino acid
<223> OTHER INFORMATION: Description of Artificial Sequence: IL-11
      binding peptide

<400> SEQUENCE: 9

Ser Ile Leu Arg Pro Asp Pro Pro Gln Gly Leu Arg Val Glu Ser Val
 1               5                  10                  15

Pro Xaa Xaa Xaa Tyr Pro
            20

<210> SEQ ID NO 10
<211> LENGTH: 7
<212> TYPE: PRT
<213> ORGANISM: Mus musculus

<400> SEQUENCE: 10

Arg Arg Leu His Ala Ser Trp
 1               5

<210> SEQ ID NO 11
<211> LENGTH: 422
<212> TYPE: PRT
```

-continued

<213> ORGANISM: Homo sapiens

<400> SEQUENCE: 11

```
Met Ser Ser Cys Ser Gly Leu Ser Arg Val Leu Ala Val Ala
 1               5                  10                  15
Thr Ala Leu Val Ser Ala Ser Pro Cys Pro Gln Ala Trp Gly Pro
             20                  25                  30
Pro Gly Val Gln Tyr Gly Gln Pro Gly Arg Ser Val Lys Leu Cys Cys
             35                  40                  45
Pro Gly Val Thr Ala Gly Asp Pro Val Ser Trp Phe Arg Asp Gly Glu
         50                  55                  60
Pro Lys Leu Leu Gln Gly Pro Asp Ser Gly Leu Gly His Glu Leu Val
 65                  70                  75                  80
Leu Ala Gln Ala Asp Ser Thr Asp Glu Gly Thr Tyr Ile Cys Gln Thr
                 85                  90                  95
Leu Asp Gly Ala Leu Gly Gly Thr Val Thr Leu Gln Leu Gly Tyr Pro
            100                 105                 110
Pro Ala Arg Pro Val Val Ser Cys Gln Ala Ala Asp Tyr Glu Asn Phe
            115                 120                 125
Ser Cys Thr Trp Ser Pro Ser Gln Ile Ser Gly Leu Pro Thr Arg Tyr
        130                 135                 140
Leu Thr Ser Tyr Arg Lys Lys Thr Val Leu Gly Ala Asp Ser Gln Arg
145                 150                 155                 160
Arg Ser Pro Ser Thr Gly Pro Trp Pro Cys Pro Gln Asp Pro Leu Gly
                165                 170                 175
Ala Ala Arg Cys Val Val His Gly Ala Glu Phe Trp Ser Gln Tyr Arg
            180                 185                 190
Ile Asn Val Thr Glu Val Asn Pro Leu Gly Ala Ser Thr Arg Leu Leu
            195                 200                 205
Asp Val Ser Leu Gln Ser Ile Leu Arg Pro Asp Pro Pro Gln Gly Leu
        210                 215                 220
Arg Val Glu Ser Val Pro Gly Tyr Pro Arg Arg Leu Arg Ala Ser Trp
225                 230                 235                 240
Thr Tyr Pro Ala Ser Trp Pro Cys Gln Pro His Phe Leu Leu Lys Phe
                245                 250                 255
Arg Leu Gln Tyr Arg Pro Ala Gln His Pro Ala Trp Ser Thr Val Glu
            260                 265                 270
Pro Ala Gly Leu Glu Glu Val Ile Thr Asp Ala Val Ala Gly Leu Pro
        275                 280                 285
His Ala Val Arg Val Ser Ala Arg Asp Phe Leu Asp Ala Gly Thr Trp
    290                 295                 300
Ser Thr Trp Ser Pro Glu Ala Trp Gly Thr Pro Ser Thr Gly Thr Ile
305                 310                 315                 320
Pro Lys Glu Ile Pro Ala Trp Gly Gln Leu His Thr Gln Pro Glu Val
                325                 330                 335
Glu Pro Gln Val Asp Ser Pro Ala Pro Pro Arg Pro Ser Leu Gln Pro
            340                 345                 350
His Pro Arg Leu Leu Asp His Arg Asp Ser Val Glu Gln Val Ala Val
        355                 360                 365
Leu Ala Ser Leu Gly Ile Leu Ser Phe Leu Gly Leu Val Ala Gly Ala
    370                 375                 380
Leu Ala Leu Gly Leu Trp Leu Arg Leu Arg Arg Gly Gly Lys Asp Gly
385                 390                 395                 400
```

```
Ser Pro Lys Pro Gly Phe Leu Ala Ser Val Ile Pro Val Asp Arg Arg
            405                 410                 415
Pro Gly Ala Pro Asn Leu
            420
```